United States Patent
Suzuki et al.

(10) Patent No.: US 7,754,236 B2
(45) Date of Patent: Jul. 13, 2010

(54) PATCH WITH IMPROVED ANCHORING PROPERTIES BETWEEN A SUBSTRATE AND AN ADHESIVE

(75) Inventors: Tatsuaki Suzuki, Tsukuba (JP); Tetsuro Tateishi, Tsukuba (JP); Naruhito Higo, Tsukuba (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 1476 days.

(21) Appl. No.: 10/517,468

(22) PCT Filed: Jun. 6, 2003

(86) PCT No.: PCT/JP03/07173

§ 371 (c)(1),
(2), (4) Date: Dec. 6, 2004

(87) PCT Pub. No.: WO03/103641

PCT Pub. Date: Dec. 18, 2003

(65) Prior Publication Data

US 2005/0175676 A1    Aug. 11, 2005

(30) Foreign Application Priority Data

Jun. 7, 2002  (JP) .............................. 2002-167514

(51) Int. Cl.
*A61F 13/00* (2006.01)
(52) U.S. Cl. ..................................... 424/449
(58) Field of Classification Search ................ 424/402, 424/404, 443, 445, 446, 447, 448, 449; 514/352; 602/58; *A61F 13/02; A61L 9/70*
See application file for complete search history.

(56) References Cited

U.S. PATENT DOCUMENTS

| 4,559,256 | A | 12/1985 | Matsumoto | |
|---|---|---|---|---|
| 4,645,502 | A | 2/1987 | Gale et al. | |
| 5,478,567 | A | 12/1995 | Nakagawa et al. | ........... 424/449 |
| 6,001,205 | A | 12/1999 | Mauro | ........... 156/153 |
| 6,129,929 | A * | 10/2000 | Wick | ........... 424/448 |
| 6,139,866 | A * | 10/2000 | Chono et al. | ........... 424/443 |
| 6,563,195 | B1 * | 5/2003 | Tomaru et al. | ........... 257/620 |

FOREIGN PATENT DOCUMENTS

| CN | 1087515 | | 6/1994 |
|---|---|---|---|
| CN | 1190618 | A | 8/1998 |
| CN | 1193275 | A | 9/1998 |
| EP | 07-138154 | | 5/1995 |
| EP | 1 074 251 | A1 | 7/2001 |
| JP | 1-83029 (U) | | 2/1989 |
| JP | 5-8339 | | 1/1993 |
| JP | 06-035381 | | 2/1994 |
| JP | 06-098931 | | 4/1994 |
| JP | 06-287134 | A * | 10/1994 |
| JP | 2816765 | | 8/1998 |
| JP | 2002-263130 | | 9/2002 |
| JP | 2002-363069 | | 12/2002 |
| WO | WO99/53906 | | 10/1999 |

OTHER PUBLICATIONS

Machine translation of JP 06-287134.*

* cited by examiner

*Primary Examiner*—Robert A Wax
*Assistant Examiner*—Jeffrey T Palenik
(74) *Attorney, Agent, or Firm*—Licata & Tyrrell P.C.

(57) ABSTRACT

The present invention relates to a patch which is free from any migration of a drug into a substrate and has favorable anchoring properties between the substrate and adhesive layer, in which the drug containing adhesive layer firmly adheres onto the substrate and which gives no adhesion residue when applied to the skin and then peeled off. Namely, a patch comprising a substrate made of a polyester-based film and a drug-containing adhesive layer laminated thereon wherein the surface roughness (also known as "the central line mean roughness" or "Ra") of the polyester-based film surface in the side in contact with the adhesive layer is from 0.05 to 0.8 μm is provided.

13 Claims, No Drawings

PATCH WITH IMPROVED ANCHORING PROPERTIES BETWEEN A SUBSTRATE AND AN ADHESIVE

DETAILED DESCRIPTION OF THE INVENTION

1. Technical Field

The invention relates to a patch, more particularly, wherein anchoring properties are improved.

2. Background Art

As administration methods for drugs, various methods such as an oral administration, rectal administration, intracutaneous administration and intravenous administration have been known, and among them the oral administration has widely been adopted. However, in case of the oral administration, there were disadvantages that a drug is susceptible to a first-pass effect in liver after absorption of the drug and after the administration an unnecessary high blood concentration is transiently recognized, which often causes adverse effects.

Therefore, in order to dissolve these disadvantages of the oral administration, the development for percutaneous absorption preparations has actively been carried out, and the percutaneous absorption technology which can make a drug absorb efficiently into the body has conventionally been investigated in the art of patches containing drugs and medicines.

A patch is generally composed of a substrate and a drug-containing adhesive layer laminated thereon and is used in order to absorb the drug contained in the adhesive layer into the body through the skin. As for such a patch, no migration of a drug into a substrate in addition to the favorable absorbability, a firm adhesion between the substrate and the adhesive, and no adhesive residue when peeled off from the skin, that is, favorable anchoring properties are needed.

However, in case of using flexible films such as polyurethane or polyvinyl chloride type films as a substrate, migration of a drug into the substrate often occurs if preserved for a long period, anticipating the effects on a percutaneous permeable property and aging stability. In addition, when a drug is strong in a diffusion permeability, it diffuses into a substrate and gives the substrate swelling-depletion, whereby under some circumstances an expected therapeutic effect can be lost. Further, also in case of using a woven fabric or an unwoven fabric for a substrate, some adsorption of a drug to the substrate was often inevitable. Moreover, while the amount of a drug used relatively increased because the thickness of an adhesive mass increased, all the amount of the drug used could not be absorbed, therefore, there was a lot of waste, and it could not hardly be said that the drug could efficiently be used. And, when expensive drugs were used, it became further uneconomical, since the drugs could not be used effectively. As a solution to inhibit the migration of these drugs to substrates and to effectively utilize the drugs, there is a method to use polyester-based films such as polyethylene terephthalate for the substrates, in which the migration of the drugs is not observed.

However, although polyester-based films, in particular, a polyethylene terephthalate films are preferably used in view of inhibition of the migration of a drug into a substrate, in case of using these in a film type there was the problem that an anchoring property between said film and an adhesive layer was bad. Therefore, although an adhesive layer was laminated on a substrate, it did not favorably adhere and was immediately separated. In addition, even if it was not separated at all, due to a weak anchoring power between a substrate and an adhesive layer there was the case that the so-called adhesive residue remained when applied to the skin and then peeled off. Moreover, there was a case that a product value was extremely reduced, wherein a base sheet was detached between layers during storage.

Thus, in order to solve these problems, that is, in order to increase an anchoring property between a substrate and a adhesive layer, for a conventional patch is employed a method that via a primer layer having an adhesive force the adhesive layer is laminated thereon. For example, as described in JP A 7-138154 and JP B 6-35381, it is possible to firmly adhere a substrate and an adhesive layer by a physical anchoring effect due to applying various primers on a polyethylene terephthalate film or blending short fibers on the primer layer. However, also in these cases, there was a case that an undesirable interaction with a primer occurred according to a drug and discolored a primer layer and an adhesive layer into yellow or other colors, therefore, such methods extremely reduced a product value. In addition, also in case of using an anchor-coating agent, since there was a possibility that the anchor-coating agent was adsorbed to a drug, it resulted in reduction of a percutaneous absorbability, therefore, as a method to increase the anchoring property it was not yet sufficient.

In addition, according to a material of a substrate, the thickness is diverse, though in case of using the above patch for medical use, usually the applied position is the skin surface, therefore, it is necessary to give the patch characteristics such as a skin adaptability and a skin non-irritating property. Moreover, a patch used for the use is often stuck for a relatively long period of time, and one which does not cause an uncomfortable feeling or an irritating feeling toward the skin after sticking on a skin surface is desired.

Moreover, if the thickness of a substrate is too thick, there is an uncomfortable feeling at the time of skin-sticking and a possibility that a patch itself injures the skin. Further, the patch becomes easy to come off against a small movement of the skin, generating a problem that an expected therapeutic effect can not be obtained. Although it is possible that the thickness of a substrate is made thin in order to solve these problems, being too much thin makes the patch itself flabby, producing the entwinement and wrinkle of the patch, and a handling property at the time of preservation and sticking operation becomes extremely bad.

Further, in case of using these in a film type, various problems occur on the handling property of a patch due to its bending stiffness. In a case that the bending stiffness of a substrate is small, the patch gets twisted and entwined when sticking it to the skin, and wrinkled after sticking, making the handling property difficult. On the contrary, a patch becomes hard as the bending stiffness becomes large, generating problems such as hurting the finger with a side edge of the patch and making it difficult to stick according to an irregularity of a sticking position of the human body. In addition, adaptability to the skin becomes insufficient, and it becomes easy to come off for a small movement. The problems of such bad handling are important problems particularly for aged patients.

Although in JP A 6-98931 is disclosed a technique to make a handling property at the time sticking favorable with an adhesive sheet in which L, the length of the long side of the adhesive sheet, X, the bending stiffness (Cantilever method) of the adhesive sheet removed a release liner, and Y, the bending stiffness of the adhesive sheet covered with the release liner, satisfy the condition of $0.5Y \geq 0.1L \geq X$. In this sheet, X, the bending stiffness of the adhesive sheet removed release liner, is not more than 10 mm, therefore, it is insufficient for improving the practical handling properties in view of the size of a normal patch for external-use. In addition, although many attempts have been carried out to improve the handling properties by furnishing an easily removable support material on the opposite side to the adhesive layer of a substrate and peeling off the support material after sticking, they are not practical due to difficulty in a production aspect, a cost aspect, etc.

Consequently, even if these methods were used, the above problems were not avoided.

DISCLOSURE OF THE INVENTION

Thus, the object of the invention is to solve the problems of the prior arts as described above and to provide a patch which is free from any migration of a drug into a substrate and shows favorable anchoring properties between the substrate and an adhesive layer, in which the drug-containing adhesive layer is firmly adhered onto the substrate and which remains no adhesive residue when applied to the skin and then peeled off.

As a result of extensive researches made to solve the above objects, the inventors surprisingly found out that anchoring properties between a substrate and an adhesive layer is improved by using a polyester-based film having the surface roughness of a specially fixed value and using the polyester-based film which is sandblasted, and accomplished the invention.

Namely, the invention relates to a patch comprising a substrate made of a polyester-based film and a drug-containing adhesive layer laminated thereon, wherein the surface roughness (Ra) of the polyester-based film surface on the side in contact with the adhesive layer is from 0.05 to 0.8 µm.

Further, the invention relates to the above patch comprising a substrate made of a polyester-based film and a drug-containing adhesive layer laminated thereon, wherein the surface of the polyester-based film surface on the side in contact with the adhesive layer is sandblasted.

Also, the invention relates to the above patch, wherein the thickness of the polyester-based film is from 5 to 40 µm.

Further, the invention relates to the above patch, wherein the thickness of the adhesive layer is from 50 to 125 µm.

Also, the invention relates to the above patch, wherein the polyester-based film is polyethylene terephthalate.

Further, the invention relates to the above patch, wherein the adhesive contains styrene-isoprene-styrene block copolymer.

Also, the invention relates to the above patch wherein the adhesive contains two components of polyisobutylene and styrene-isoprene-styrene block copolymer.

Further, the invention relates to the above patch, wherein the adhesive contains a tackifying agent and/or a plasticizer.

Also, the invention relates to the above patch, wherein the area is from 5 to 60 $cm^2$.

Further, the invention relates to the above patch, wherein the bending stiffness of a substrate is from 10 to 80 mm.

Also, the invention relates to the above patch, wherein the drug is a narcotic analgesic agent.

Further, the invention relates to the above patch, wherein the narcotic analgesic agent is fentanyl or salts thereof.

According to the invention, it is possible to provide a patch, wherein not only the migration of a drug into a substrate is inhibited by using a polyester-based film, but the anchoring properties are made favorable by having the surface roughness with a particularly fixed value of said film on the side in contact with a adhesive layer. Namely, no so-called adhesive residue remains when applied to the skin and then peeled off, and there is no case that a product value is extremely reduced, wherein a base sheet detaches between layers during storage. Moreover, since there is no need to set up a primer layer or to use an anchor-coating agent, interaction with a drug is not caused and problems such as discoloration are not occurred, and it is possible to make the anchoring properties improved.

Further, the patch of the invention can be extremely thinned in the thickness compared with conventional patches by making the substrate in a film type. Therefore, the patch is light and not bulky, gives no uncomfortable feeling at the time of skin-sticking compared with a thick patch and does not injure the skin, in addition, irritation to the skin is reduced, and a patch with a favorable use feeling can be provided. Further, according to the patch of the invention, the migration into a substrate can be suppressed, while an effect of a drug is efficiently obtained in a smaller area compared with conventional patches, therefore, problems such as rash is reduced due to a small adhered area, and further, reduction of a skin irritation can be achieved.

In addition, in a case that the bending stiffness of a substrate of a patch of the invention is from 10 to 80 mm, it does not get entwined or wrinkled when sticking, making it possible to provide a patch with favorable handling properties.

Moreover, although drugs such as fentanyl known as a drug with a high analgesic effect is used by a constant-rate instillation during the operation and after the operation, the effect does not sustain because a disappearance half-life is short. Therefore, as for pains sustaining for a relatively long period of time such as cancerous pain treatment with a patch which has good skin permeability as well as excellent aging stability is effective. Further, although patch preparations with a sustained effect, which contain fentanyl base, have already been commercially available in the United States, these preparations have disadvantages that irritating properties such as itchiness and rubor occur easily. However, by using a patch of the invention the patch can be provided which, as described above, has low skin irritating properties, no migration of a drug into a substrate, favorable skin absorbability, and excellent aging stability, and carries an adhesive layer containing fentanyl or salts thereof, morphine sulfate or the other narcotic analgesic agents.

MODE FOR CARRYING OUT THE INVENTION

In the following, the patch of the invention is illustrated in detail.

A patch used in the invention is one set up with a substrate and an adhesive layer, wherein said substrate is made of a polyester-based film, in addition, the side in contact with an adhesive layer of said substrate has a specially fixed surface roughness or wherein it has a surface roughness with sandblasting treatment. Moreover, the substrate is made of a polyester-based film and indicates one supporting an adhesive layer.

The patch of the invention is characterized in that the polyester-based film being a substrate has a surface roughness. By roughening said film surface, anchoring properties between the substrate and an adhesive layer is improved, making it possible to afford a patch excellent in use feeling, which gives no so-called adhesive residue when the patch is applied to the skin and then peeled off. Therefore, if such an effect is obtained, any method may be used as a method to roughen the surface, though, for example, sandblasting treatment can preferably be used. Moreover, in order to improve anchoring properties, the treatment is done so that the surface roughness (Ra) becomes 0.05-0.8 µm, preferably 0.3-0.7 µm. That is why an anchoring collapse easily occurs as the surface roughness becomes small, whereby even the substrate and the adhesive layer are laminated, they do not adhere favorably, giving a tendency that an enough anchoring power is not obtained, and on the other hand, anchoring properties is improved as the surface roughness becomes large, though pinholes tend to be made in the substrate easily.

Herein, a sandblasting treatment is a method to physically roughen a film surface by spraying sands (silica sands) on the surface of a film at high speed.

In addition, the surface roughness in the invention is based on JIS-B0601, and Ra shows the central line mean roughness (cutoff value, 0.25 mm).

A material constituting the substrate in a patch of the invention is preferably a polyester-based film from the point of view of inhibiting migration of a drug to the substrate, in particular preferably polyethylene terephthalate. Using flexible films such as polyurethane and the like shows a high possibility of migration of a drug into a substrate, though using polyester-based films such as polyethylene terephthalate does not show such migration of a drug into the substrate, making it possible to efficiently utilize the drug, and it is particularly preferable when using an expensive drug.

The thickness of the polyester-based film is not particularly limited, preferably 2-50 μm, more preferably 5-40 μm, in particular 20-30 μm. It is possible to be damaged during a preparation step and at the time of sticking the patch as the thickness is smaller and there tends to make handling difficult, such as causing pinholes easily during the step of a sandblasting treatment and wrinkling at the time of sticking the patch. On the contrary, since a patch becomes harder as the thickness becomes larger, it feels uncomfortable when it is stuck to the skin, and use feeling tends to be impaired.

The polyester-based film may be used in mono-layer or by laminating. Also, in some embodiment, a woven fabric or a nonwoven fabric may be used by laminating.

The thickness of the adhesive layer of the invention is preferably 50-125 μm. If the thickness is too thin, it is not possible to uniformly apply the adhesive layer onto the substrate, causing trouble in a preparation step, and a drug permeation speed tends to be reduced. On the contrary, if the thickness is too thick, airspaces are generated in the adhesive layer and do not give it uniformity, causing trouble in a preparation step and resulting in using a drug beyond necessity and it is likely to be wasted.

The hard and flexible degree of the substrate of the invention is preferably 10-80 mm, in particular 12-60 mm. That is why if the bending stiffness is small, a patch is entwined or wrinkled, giving a tendency that the handling makes difficult, and on the contrary, if it is too large, the patch is hard, occurring problems such as hurting the finger with a side edge of the patch and making it difficult to stick in accordance with an irregularity of a sticking position of the human body, in addition, it easily comes off for a small movement of the skin, whereby a sufficient drug effect may not be obtained due to a change of a sticking area.

A fat soluble polymer blended in the adhesive layer of the invention is not particularly limited, and preferable examples include polyisobutylene (PIB), styrene-isoprene-styrene block copolymer (SIS), isoprene rubber, styrene-butadiene-styrene block copolymer (SBS), acrylic type polymer (copolymer of at least two polymers from 2-ethylhexyl acrylate, vinyl acetate, methacrylate, methoxyethyl acrylate and acrylic acid) and the like. These may be used alone or with mixture of two or more polymers. Among these, use of two components of PIB and SIS is preferable. Moreover, in this case, weight ratio of the mixture is preferably from 1:1 to 1:4.

Considering physical properties of the preparation itself and a favorable adhesive power to the human skin, the fat-soluble polymer is include in 0.1-98 wt %, preferably in 0.1-70 wt %, more preferably in 0.1-50 wt % based on the total weight of the adhesive layer in the patch of the invention.

As a drug contained in the adhesive layer of the invention, which is not particularly limited, if it can be percutaneously absorbed, it includes, for example, hypnotic-sedative agents (flurazepam hydrochloride, rilmazafone hydrochloride, phenobarbital, amobarbital, etc.), anti-pyretic and anti-inflammatory analgesic agents (butorphanol tartarate, perisoxal citrate, acetaminophen, mefenamic acid, diclofenac sodium, aspirin, alclofenac, ketoprofen, flurbiprofen, naproxen, piroxicam, pentazocine, indomethacin, glycol salicylate, aminopyrine, loxoprofen, etc.), steroidal anti-inflammatory agents (hydrocortisone, prednisolone, dexamethasone, betamethasone, etc.), excitation-analeptic agents (methamphetamine hydrochloride, methylphenidate hydrochloride, etc.), psychotropic agents (imipramine hydrochloride, diazepam, sertraline hydrochloride, fluvoxamine maleate, paroxetine hydrochloride, citalopram hydrobromide, fluoxetine hydrochloride, alprazolam, chlorpromazine hydrochloride, etc.), hormonal agents (estradiol, estriol, progesterone, norethisterone acetate, metenolone acetate, testosterone, etc.), local anesthetic agents (lidocain hydrochloride, procaine hydrochloride, tetracaine hydrochloride, etc,), agents for urinary organs (oxybutynin hydrochloride, tamsulosin hydrochloride, etc.), skeletalmuscle relaxants (tizanidine hydrochloride, eperisone hydrochloride, pridinol mesilate, etc.), autonomic agents (carpronium chloride, neostigmine bromide, etc.), antiepleptic agents (sodium valproate, clonazepam, etc.), anti-Parkinson's disease agents (pergolide mesilate, bromocriptine mesilate, trihexyphenidyl hydrochloride, amantadine hydrochloride, ropinirole hydrochloride, cabergoline, etc.), antihistaminic agents (clemastine fumarate, diphenhydramine tannate, etc.), diuretic agents (hydrofulmetiazide, furosemide, etc.), respiratory stimulants (lobeline hydrochloride, dimorpholamine, naloxone hydrochloride, etc.), anti-migraine agents (dihydroergotamine mesilate, sumatriptan, etc.), bronchodilator agents (tulobuterol hydrochloride, procaterol hydrochloride, etc.), cardiotonic agents (isoprenaline hydrochloride, dopamine hydrochloride, etc.), coronary dilators (diltiazem hydrochloride, verapamil hydrochloride, isosorbide nitrate, nitroglycerin, etc.), peripheral vasodilators (nicametate citrate, tolazoline hydrochloride, etc.), smoking cessation aid agents (nicotine, etc.), cardiovascular agents (flunarizine hydrochloride, nicardipine hydrochloride, benidipine hydrochloride, efonidipine hydrochloride, bisoprolol fumarate, metoprolol tartarate, etc.), antiarrhythmic agents (propranolol hydrochloride, alprenolol hydrochloride, nadolol, etc.), antiallergic agents (ketotifen fumarate, azelastine hydrochloride, etc.), anti-dizziness agents (betahistine mesilate, difenidol hydrochloride, etc.), serotonin receptor antagonistic antiemetics (ondansetron hydrochloride, granisetron hydrochloride, etc.), gastrointestinal motility improving agents (domperidone, cisapride, etc.), blood glucose lowering agents (glibenclamide, tolbutamide, etc.), anorectic agents (mazindol, etc.), chemotherapeutic agents (isoniazid, ethionamide, etc.), anticoagulant (warfarin potassium, etc.), agents for Alzheimer disease (tacrine, donepezil hydrochloride, etc.), antipodagric agents (colchicine, probenecid, etc.) and narcotic analgesic agents (morphine sulfate, fentanyl citrate, etc.), and so as to obtain the effect of fentanyl and salts thereof efficiently because these drugs are particularly expensive, these drugs can be used preferably for the patch of the invention. As the salts of fentanyl, they are not limited particularly, may be inorganic or organic salts, and illustrative of representative salts of fentanyl are citrate, hydrochloride, fumarate and the like. Among these, fentanyl citrate is particularly preferable. Further, fentanyl or salts thereof may be used alone and with mixture of two or more salts thereof.

In addition, considering an enough permeation amount as a percutaneous administration preparation and a disadvantageous effects to physical properties of the preparation itself, fentanyl or salts thereof are blended preferably in an amount of 0.05-20 wt % based on the total weight of the adhesive layer in the patch of the invention.

As to the patch of the invention, a skin permeability of fentanyl or salts thereof is extremely increased by blending sodium acetate. Sodium acetate is preferably blended in 0.01-15 wt %, more preferably in 0.01-10 wt %, in particular preferably in 0.01-5 wt % based on the total weight of the adhesive layer. If the blend amount of sodium acetate is little, the effect to extremely improve the skin permeability is not fully obtained, and if it is too much, there is a tendency that the skin irritations tend to become large.

When a salt of fentanyl is fentanyl citrate, the blend weight ratio between fentanyl citrate and sodium acetate may be blended, which can give effects in aspects of physical properties and the skin permeability, though the maximum effects are obtained typically in case of 2:1. If the blend ratio of sodium acetate is small, the skin permeability of the drug is abruptly reduced, and on the contrary, if the blend ratio of sodium acetate is large, giving a non uniform preparation, and physical properties such as adhesiveness tend to get worth.

Further, when a salt of fentanyl is fentanyl acetate, blend of sodium acetate is not mandatory because a similar effect to blend of sodium acetate can be obtained.

Further, since the adhesiveness of a fat soluble polymer is low, a tackifying agent may be blended in an adhesive layer of the preparation to give the adhesiveness to the preparation. As tackifying agents, illustrative of preferable examples are agents such as a poly-terpene resin, petroleum resin, rosin, rosin ester and fat soluble phenol resin types. The tackifying agent is preferably blended in an amount of 0.1-70 wt %, more preferably in 5-50 wt %, in particular in 10-35 wt % based on the total weight of the adhesive layer in the preparation of the invention.

Also, in order to improve processing properties and adjust adhesiveness of the patch of the invention, fat may be blended in the adhesive layer as a plasticizer. As fat preferable are liquid paraffin, squalane, olive oil, camellia oil, persic oil, peanut oil and the like. In particular, liquid paraffin is preferred.

The fat is preferably blended in an amount of 1.0-70 wt %, more preferably in 10-60 wt %, in particular in 20-50 wt % based on the total weight of the adhesive layer in the preparation of the invention.

In addition, if necessary, an absorption enhancer may be blended into the adhesive layer in the preparation of the invention. As an absorption enhancer, any compound of which an absorption enhancing effect on the skin is known may be used. Examples include $C_6$-$C_{20}$ fatty acids, fatty alcohols, fatty acid esters or ethers, aromatic organic acids, aromatic alcohols, aromatic organic acid esters or ethers. Furthermore, examples include lactic acid esters, acetic acid esters, monoterpene compounds, sesquiterpene compounds, Azones or derivatives thereof, glycerol fatty acid esters, sorbitan fatty acid esters, polysorbates, polyethlene glycol fatty acid esters, polyoxyethylene hardened castor oils, sucrose fatty acid esters and the like. Specifically, caprylic acid, capric acid, caproic acid, lauric acid, myristic acid, palmitic acid, stearic acid, oleic acid, linoleic acid, linolenic acid, lauryl alcohol, myristyl alcohol, oleyl alcohol, cetyl alcohol, methy laurate, isopropyl myristate, myristyl myristate, octyl-dodecyl myristate, cetyl palmitate, salicylic acid, methyl salicylate, ethylene glycol salicylate, cinnamic acid, methyl cinnamate, cresol, cetyl lactate, ethyl acetate, propyl acetate, geraniol, thymol, eugenol, terpineol, 1-menthol, borneol, d-limonene, isoeugenol, isoborneol, nerol, dl-camphor, glycerol monolaurate, glycerol monooleate, sorbitan monolaurate, sucrose monolaurate, polysorbate 20, polyethylene glycol monolaurate, polyethylene glycol monostearate, HCO-60 (hardened caster oil), and 1-[2-(decylthio)ethyl]aza-cyclopentan-2-one (hereafter abbreviated as pyrothiodecane) are preferred, and in particular, lauryl alcohol, myristyl alcohol, ethylene glycol salicylate and pyrothiodecane are preferred.

Such absorption enhancers may be blended in an amount of preferably 0.01-20 wt %, more preferably 0.1-10 wt % and in particular 0.5-5 wt % based on the total weight of the adhesive layer in the preparation of the invention. If the amount of the absorption enhancer is too much, skin irritations such as rubor and edema occurs, and if it is too little, an effect of blending the absorption enhancer tends not to be obtained.

Further, in the patch of the invention, a hydrophilic polymer may be blended, if required, in order to absorb aqueous components such as sweat from the skin. As the hydrophilic polymer preferable are, for example, light anhydrous silicic acid, cellulose derivatives [carboxymethyl cellulose (CMC), sodium carboxymethyl cellulose (CMCNa), methyl cellulose (MC), hydroxypropylmethyl cellulose (HPMC), hydroxypropyl cellulose (HPC), hydroxyethyl cellulose (HEC), starch derivatives (pullulan), polyvinyl alcohol (PVA), polyvinylpyrrolidone (PVP), vinyl acetate (VA), carboxyvinyl polymer (CVP), ethylvinyl acetate (EVA), Eudragit (trade name), gelatin, polyacrylic acid, sodium polyacrylate, polyisobutylene-maleic anhydride copolymer, alginic acid, sodium alginate, carrageenan, Arabian gum, tragacanth gum, karaya gum and polyvinyl methacrylate. In particular, light anhydrous silicic acid, cellulose derivatives (CMCNa, HPMC, HPC, MC) and Eudragit are preferred.

The hydrophilic polymer may be blended in an amount of preferably 0.01-20 wt %, and in particular preferably 0.5-10 wt % based on the total weight of the adhesive layer in the patch of the invention.

In addition, the other components such as a cross-linking agent, preservative and antioxidant may be blended in the adhesive layer in the patch of the invention.

As cross-linking agents, thermosetting resins such as amino resins, phenol resins, epoxy resins, alkyd resins and unsaturated polyesters, isocyanate compounds, block isocyanate compounds, organic cross-linking agents, and inorganic cross-linking agents such as metals or metal compounds, are preferable. As preservatives, ethyl p-hydroxy benzoate, propyl p-hydroxy benzoate, butyl p-hydroxy benzoate and the like are preferable. As antioxidants, tocopherol and its ester derivatives, ascorbic acid, ascorbic acid-stearic acid ester, nordihydroguaretic acid, dibutyl hydroxy toluene (BHT), butyl hydroxy anisole (BHA) and the like are preferable.

Further, the adhesive layer in the patch of the invention preferably consists of a nonaqueous base, whereby the effect of the invention can be obtained by the nonaqueous base.

The adhesive layer having the composition described above may be prepared by any method. For example, in case of preparing by a solvent method, the other components are added to an organic solvent solution of a blended polymer and stirred, and then the mixture is spread on the substrate and dried to give the preparation. Moreover, in a case that a blended polymer can be coated by a hot-melt method, the polymer component is dissolved at high temperature, then added with the other components, stirred, and spread on the substrate to give the patch of the invention.

In addition, the area of the patch of the invention is not particularly limited if it is enough to obtain a sufficient effect of a drug, though it is preferably 5-60 cm². That is why if the area is too small, a sufficient effect of a drug can not be obtained, and on the contrary, if it is too large, it can hardly follow a skin movement and makes handling difficult, in addition, a skin irritation such as rash is likely to increase due to the large sticking area.

Moreover, the patch of the invention may be colored by kneading a pigment into the substrate without particular limitation. For example, addition of titanium oxide can give a white substrate. By giving such a white color, letters or the like are easily printed on a substrate surface, therefore, also in case of using a drug which needs caution in the handling, a caution item or the like can clearly be printed. Further, even in case of coloring by use of titanium oxide no problem occurs in solvent resistance, the stability being favorable.

In addition, the other constituting components in the patch of the invention are not particularly limited, if the adhesive layer is constituted with the above composition. For example, the patch of the invention can consist of the adhesive layer, the substrate layer supporting it, and further, a removable-paper set on the adhesive layer and the like. As to the removable-paper, films such as polyester treated with silicone, polyvinyl chloride and polyvinylidene chloride, and a high-quality paper treated with silicone may be used.

EXAMPLE

In the following, the invention is explained in more detail by the examples. The invention, however, is not limited to these examples, and various changes may be made without departing from the scope of the invention. In the examples, '%' means '% by weight'.

Example 1-1

| | |
|---|---|
| Sodium acetate | 1.5% |
| Liquid paraffin | 42.0% |
| Poly-terpene resin tackifying agent (manufactured by Arakawa Kagaku Kogyo Co. Arcon P-100) | 29.5% |
| PIB (mixture of Vistanex MM-L-100 of 1.5% and Vistanex LMMH of 6.0%) | 7.5% |
| SIS (SIS-5002) | 16.5% |
| Aluminum silicate | 0.5% |
| Fentanyl citrate | 3.0% |
| Total amount | 100% |

In the composition, the components except sodium acetate and fentanyl citrate were dissolved and mixed at 180° C., then added with the remaining components, followed by dispersion till the mixture became uniform, and then the mixture was spread on PET film of 25 μm so that the adhesive layer became 50 μm to obtain the patch of the invention by the conventional method. Further, the PET film was sandblasted on the one side in advance in such a manner that the surface roughness (Ra) became 0.1 μm.

Example 1-2

In the same composition as that of the example 1-1, the mixture was spread on PET film of 10 μm so that the adhesive layer became 50 μm to obtain the patch of the invention by the conventional method. Further, the PET film was sandblasted on the one side in advance in such a manner that the surface roughness (Ra) became 0.1 μm.

Example 1-3

In the same composition as that of the example 1-1, the mixture was spread on PET film of 3.5 μm so that the adhesive layer became 50 μm to obtain the patch of the invention by the conventional method. Further, the PET film was sandblasted on the one side in advance in such a manner that the surface roughness (Ra) became 0.1 μm.

Example 2-1

In the same composition as that of the example 1-1, the mixture was spread on PET film of 25 μm so that the adhesive layer became 50 μm to obtain the patch of the invention by the conventional method. Further, the PET film was sandblasted on the one side in advance in such a manner that the surface roughness (Ra) became 0.3 μm.

Example 2-2

In the same composition as that of the example 1-1, the mixture was spread on PET film of 10 μm so that the adhesive layer became 50 μm to obtain the patch of the invention by the conventional method. Further, the PET film was sandblasted on the one side in advance in such a manner that the surface roughness (Ra) became 0.3 μm.

Example 2-3

In the same composition as that of the example 1-1, the mixture was spread using PET film of 40 μm so that the adhesive layer became 50 μm to obtain the patch of the invention by the conventional method. Further, the PET film was sandblasted on the one side in advance in such a manner that the surface roughness (Ra) became 0.3 μm.

Example 3-1

In the same composition as that of the example 1-1, the mixture was spread using PET film of 25 μm so that the adhesive layer became 50 μm to obtain the patch of the invention by the conventional method. Further, the PET film was sandblasted on the one side in advance in such a manner that the surface roughness (Ra) became 0.6 μm.

Example 3-2

In the same composition as that of the example 1-1, the mixture was spread on PET film of 10 μm so that the adhesive layer became 50 μm to obtain the patch of the invention by the conventional method. Further, the PET film was sandblasted on the one side in advance in such a manner that the surface roughness (Ra) became 0.6 μm.

Example 3-3

In the same composition as that of the example 1-1, the mixture was spread using PET film of 50 μm so that the adhesive layer became 50 μm to obtain the patch of the invention by the conventional method. Further, the PET film was sandblasted on the one side in advance in such a manner that the surface roughness (Ra) became 0.6 μm.

Comparative Example 1-1

In the same composition as that of the example 1-1, the mixture was spread using PET film of 25 μm so that the adhesive layer became 50 μm to obtain a patch by the conventional method. Further, the PET film was sandblasted on the one side in advance in such a manner that the surface roughness (Ra) became 0.01 μm.

Comparative Example 1-2

In the same composition as that of the example 1-1, the mixture was spread using PET film of 10 μm so that the adhesive layer became 50 μm to obtain a patch by the conventional method. Further, the PET film was sandblasted on the one side in advance in such a manner that the surface roughness (Ra) became 0.01 μm.

Comparative Example 2-1

In the same composition as that of the example 1-1, the mixture was spread using PET film of 25 μm so that the adhesive layer became 50 μm to obtain a patch by the conventional method. Further, the PET film was sandblasted on the one side in advance in such a manner that the surface roughness (Ra) became 1.0 μm.

Comparative Example 2-2

In the same composition as that of the example 1-1, the mixture was spread using PET film of 10 μm so that the adhesive layer became 50 μm to obtain a patch by the conventional method. Further, the PET film was sandblasted on the one side in advance in such a manner that the surface roughness (Ra) became 1.0 μm.

Comparative Example 3-1

In the same composition as that of the example 1-1, the mixture was spread using PET film of 25 μm so that the adhesive layer became 50 μm to obtain a patch by the conventional method. Further, the PET film was sandblasted on the one side in advance in such a manner that the surface roughness (Ra) became 1.3 μm.

Comparative Example 3-2

In the same composition as that of the example 1-1, the mixture was spread using PET film of 10 μm so that the adhesive layer became 50 μm to obtain a patch by the conventional method. Further, the PET film was sandblasted on the one side in advance in such a manner that the surface roughness (Ra) became 1.3 μm.

Then, the evaluation tests as shown in the following were carried out using each patch of the examples and the comparative examples.

(Anchoring Property Test)

The following anchoring property tests were carried out using the patches of examples 1-1, 2-1 and 3-1 and the comparative examples 1-1, 2-1 and 3-1. The experimental method was to stick each patch to 10 persons for 8 hours and to carry out a removal operation after sticking of 8 hours, evaluating presence or absence of anchoring collapse (detachment between the substrate and the adhesive layer).

TABLE 1

|  | Surface Roughness Ra (μm) | Anchoring properties |
|---|---|---|
| Example 1-1 | 0.1 | ○ |
| Example 2-1 | 0.3 | ○ |
| Example 3-1 | 0.6 | ○ |
| Comparative example 1-1 | 0.01 | X |
| Comparative example 2-1 | 1.0 | ○ |
| Comparative example 3-1 | 1.3 | ○ |

(PET 25 μm)

(Evaluation Standard)

Anchoring properties

○: No observation of anchoring collapse for all the members

Δ: Observation of anchoring collapse for 1-3 persons

X: Observation of anchoring collapse for not less than 4 persons (Presence or Absence of Substrate Pinhole)

The test on presence or absence of pinholes in the substrate on each thickness of the examples and comparative examples was carried out. Ten sheets of films of 30 cm×30 cm were evaluated with the naked eye, and even if at least one pinhole was found, it was counted that there was a pinhole. The results are shown in Table 2.

TABLE 2

| | Surface roughness Ra (μm) | Thickness of films (μm) | Substrate pinhole |
|---|---|---|---|
| Example 1-1 | 0.1 | 25 | ○ |
| Example 1-2 | | 10 | ○ |
| Example 1-3 | | 3.5 | ○ |
| Example 2-1 | 0.3 | 25 | ○ |
| Example 2-2 | | 10 | ○ |
| Example 2-3 | | 40 | ○ |
| Example 3-1 | 0.6 | 25 | ○ |
| Example 3-2 | | 10 | ○ |
| Example 3-3 | | 50 | ○ |
| Comparative example 1-1 | 0.01 | 25 | ○ |
| Comparative example 1-2 | | 10 | ○ |
| Comparative example 2-1 | 1.0 | 25 | X |
| Comparative example 2-2 | | 10 | X |
| Comparative example 3-1 | 1.3 | 25 | X |
| Comparative example 3-2 | | 10 | X |

Substrate pinhole . . . ○: Absence, X: Presence (Use Feeling Test)

As to each thickness in the examples 1 2 and 3, use feeling test was carried out. The experimental method was to stick to 10 persons for 24 hours and to evaluate use feeling. The results are shown in Table 3.

TABLE 3

| | Thickness of films (μm) | Use feeling (persons/10) | | | Stickiness (persons/10) | |
|---|---|---|---|---|---|---|
| | | Not uncomfortable | Little bit uncomfortable | Uncomfortable | Sticky | Non Sticky |
| Example1-1 | 25 | 10 | 0 | 0 | 10 | 0 |
| Example1-2 | 10 | 10 | 0 | 0 | 10 | 0 |
| Example1-3 | 3.5 | 10 | 0 | 0 | 5 | 5 |
| Example2-3 | 40 | 9 | 1 | 0 | 10 | 0 |
| Example3-3 | 50 | 3 | 4 | 3 | 8 | 2 |

As is evident from Table 1, in the adhesive tapes with the surface roughness of the examples 1-3 no so-called adhesive residue was observed when applied to the skin and then peeled off, showing favorable anchoring properties. On the contrary, when the surface roughness is too small, the anchoring property becomes unfavorable, and as is evident from Table 2, when the surface roughness is too large, the anchoring property is favorable, though pinholes are generate in the substrate. Therefore, in order to get preferable anchoring property and in order not to generate pinholes in the substrate, the surface roughness (Ra) is preferably 0.05-0.8 μm which is the condition that is consistent with both. Compared with the comparative examples 1-3, the examples 1-3 generate no pinhole in the substrates, giving the excellent patches with favorable anchoring properties.

Further, as is evident from Table 3, in the cases of the examples 2-3 and 3-3, in which the thickness of the films is thick, the surface roughness is the same as that of the examples 2-1 and 3-1, respectively, therefore, no problem occurs for the anchoring properties and the use feeling, though they tend to be difficult to be stuck to the skin because the patches are entwined and wrinkled. Therefore, although as the thickness of the polyester-based monolayer film, that of about 2-50 μm can preferably be used, that of 5-40 μm is more preferable from aspects that both of use feeling and ease of sticking are favorable.

INDUSTRIAL APPLICABILITY

According to the invention, a patch, which shows favorable anchoring properties and excellent handling properties can be provided.

The invention claimed is:

1. A patch comprising a substrate made of a polyester-based film and a drug-containing adhesive layer laminated thereon, wherein a side of said polyester-based film surface in contact with said drug-containing adhesive has a surface roughness (Ra) of from 0.05 to 0.8 μm thereby increasing anchoring between said polyester-based film and said drug anchoring adhesive layer without producing pinholes in said substrate.

2. The patch of claim 1, wherein the thickness of the polyester-based film is from 5 to 25 μm.

3. The patch of claim 1, wherein the thickness of the adhesive layer is from 50 to 125 μm.

4. The patch of claim 1, wherein the polyester-based film is polyethylene terephthalate.

5. The patch of claim 1, wherein the adhesive contains styrene-isoprene-styrene block copolymer.

6. The patch of claim 1, wherein the adhesive contains two components of polyisobutylene and styrene-isoprene-styrene block copolymer.

7. The patch of claim 1, wherein the adhesive contains a tackifying agent or a plasticizer or a tackifying agent and a plasticizer.

8. The patch of claim 1, wherein the area is from 5 to 60 cm$^2$.

9. The patch of claim 1, wherein the bending stiffness of a substrate is from 10 to 80 mm.

10. The patch of claim 1, wherein the drug is a narcotic analgesic agent.

11. The patch of claim 10, wherein the narcotic analgesic agent is fentanyl or salts thereof.

12. The patch of claim 1 wherein the side of said polyester-based film surface in contact with said drug-containing adhesive is sandblasted prior to contact with said drug containing adhesive layer.

13. The patch of claim 1, wherein the thickness of the polyester-based film is from 5 to 10 μm.

* * * * *